United States Patent
Roy et al.

(10) Patent No.: US 12,226,736 B2
(45) Date of Patent: Feb. 18, 2025

(54) IN VIVO BLOOD FILTRATION MEMBRANES AND DEVICES

(71) Applicant: The Regents of the University of California, Oakland, CA (US)

(72) Inventors: Shuvo Roy, San Ramon, CA (US); Benjamin W. Chui, Sunnyvale, CA (US); Nathan Wright, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1077 days.

(21) Appl. No.: 17/055,326

(22) PCT Filed: May 17, 2019

(86) PCT No.: PCT/US2019/032919
§ 371 (c)(1),
(2) Date: Nov. 13, 2020

(87) PCT Pub. No.: WO2019/222661
PCT Pub. Date: Nov. 21, 2019

(65) Prior Publication Data
US 2021/0229038 A1    Jul. 29, 2021

Related U.S. Application Data

(60) Provisional application No. 62/781,909, filed on Dec. 19, 2018, provisional application No. 62/751,363, (Continued)

(51) Int. Cl.
*B01D 61/18* (2006.01)
*A61M 1/16* (2006.01)
(Continued)

(52) U.S. Cl.
CPC .............. *B01D 61/28* (2013.01); *A61M 1/16* (2013.01); *A61M 1/1621* (2014.02);
(Continued)

(58) Field of Classification Search
CPC ........ B01D 61/18; B01D 61/28; B01D 69/02; B01D 69/06; B01D 2221/10;
(Continued)

(56) References Cited

U.S. PATENT DOCUMENTS

| 3,370,710 A | 2/1968 | Bluemle, Jr. |
| 2003/0205552 A1 | 11/2003 | Hansford et al. |

(Continued)

FOREIGN PATENT DOCUMENTS

| CN | 105025424 | 11/2015 |
| WO | 2017192556 | 11/2017 |
| WO | 2018237036 | 12/2018 |

OTHER PUBLICATIONS

Chui et al. (2018) Robust 'Ribbed' Nanoporous Membranes for Implantable Bio-Artificial Kidneys Solid-State Sensors, Actuators and Microsystems Workshop, Jun. 3-7, 2018 retrieved on Jul. 8, 2019). pp. 98-99.

(Continued)

*Primary Examiner* — John Kim
(74) *Attorney, Agent, or Firm* — Edward J. Baba; Michael J. Blessent; Bozicevic, Field & Francis LLP

(57) ABSTRACT

Filtration membrane with improved mechanical stability and increased resistance to pressure is provided. The filtration membrane is useful for in vivo implantable filtration devices, such as, an artificial kidney. In vivo implantable filtration devices are also provided.

12 Claims, 18 Drawing Sheets

Related U.S. Application Data filed on Oct. 26, 2018, provisional application No. 62/673,645, filed on May 18, 2018.

(51) Int. Cl.
*A61M 1/34* (2006.01)
*B01D 61/28* (2006.01)
*B01D 69/02* (2006.01)
*B01D 69/06* (2006.01)

(52) U.S. Cl.
CPC ............ *A61M 1/1678* (2013.01); *A61M 1/34* (2013.01); *B01D 61/18* (2013.01); *B01D 69/02* (2013.01); *B01D 69/06* (2013.01); *B01D 2221/10* (2013.01); *B01D 2323/28* (2013.01); *B01D 2325/021* (2013.01); *B01D 2325/08* (2013.01)

(58) Field of Classification Search
CPC .......... B01D 2323/28; B01D 2325/021; B01D 2325/08; B01D 67/0032; A61M 1/16; A61M 1/1621; A61M 1/1678; A61M 1/34; A61M 2207/00
See application file for complete search history.

(56) References Cited

U.S. PATENT DOCUMENTS

| | | |
|---|---|---|
| 2012/0183946 A1 | 4/2012 | Tang et al. |
| 2012/0289881 A1 | 11/2012 | Lyu et al. |
| 2015/0090661 A1 | 4/2015 | Kant et al. |
| 2016/0007119 A1 | 1/2016 | Harrington |
| 2016/0332119 A1 | 11/2016 | Fissell et al. |
| 2020/0114058 A1* | 4/2020 | Roy ..................... A61M 5/165 |

OTHER PUBLICATIONS

Fissell et al.(2009) "The Implantable Artificial Kidney" Semin. Dial. 22(6): 665-70.

Kim et al.(2016) "Diffusive Silicon Nanopore Membranes for Hemodialysis Applications," PLoS One. 11(7): e0159526.

Roy et al.(2009) "Silicon Nanopore Membrane Technology for an Implantable Artificial Kidney." Proceedings of Transducers, Denver, CO, USA.

* cited by examiner

IN VIVO BLOOD FILTRATION MEMBRANES AND DEVICES

CROSS-REFERENCE TO RELATED APPLICATIONS

This application claims the benefit of U.S. Provisional patent Application Ser. No. 62/673,645 filed May 18, 2018, U.S. Provisional patent Application Ser. No. 62/751,363 filed Oct. 26, 2018, and U.S. Provisional Patent Application Ser. No. 62/781,909 filed Dec. 19, 2018 the disclosures of which application are herein incorporated by reference in their entirety.

STATEMENT REGARDING FEDERALLY SPONSORED RESEARCH

This invention was made with government support under grant nos. U01 EB021214 and U01 EB025136 awarded by the National Institutes of Health. The government has certain rights in the invention.

INTRODUCTION

An implantable filtration device is the goal for treatments aimed at eliminating ex vivo blood filtration, such as, dialysis. While significant effort has been put into developing the individual components of such a device, there is room for improvements, such as, improvement in filtration rates and/or increase in mechanical stability of the filtration membrane device.

SUMMARY

Filtration membrane with improved mechanical stability and increased resistance to pressure is provided. The filtration membrane is useful for in vivo implantable filtration devices, such as, an artificial kidney. Clinical scale filtration devices and method for making the same are also provided.

BRIEF DESCRIPTION OF THE FIGURES

FIG. 7A. Blood filtration device having parallel silicone nanopore membranes for blood filtration with a cut-away section to reveal blood flow path. FIG. 7B. Blood flow path in the stacked membrane filter configuration.

FIG. 17a. Arrow pointing to polycarbonate housing. FIG. 17b. Arrow pointing to SNM chips. FIG. 17c. Arrow pointing to silicone bonding layers. Thicker silicone bonding layers placed along long edges of the SNM chips form blood flow path between the SNM chips, and thinner silicone bonding layers placed discontinuously along long and short edges of the SNM chips, as well as on interior surfaces of the SNM chips (see also FIG. 10) form flow path for ultrafiltrate. FIG. 17d. Arrow pointing to epoxy attaching SNM chips to housing.

FIG. 18a. Arrow pointing to polycarbonate housing. FIG. 18b. Arrow pointing to SNM chips. FIG. 18c. Arrow pointing to silicone bonding layers. Thicker silicone bonding layers placed along long edges of the SNM chips form blood flow path between the SNM chips, and thinner silicone bonding layers placed discontinuously along long and short edges of the SNM chips, as well as on interior surfaces of the SNM chips (see also FIG. 10) form flow path for ultrafiltrate. FIG. 18d. Arrow pointing to epoxy attaching SNM chips to housing.

DEFINITIONS

Figure 1:
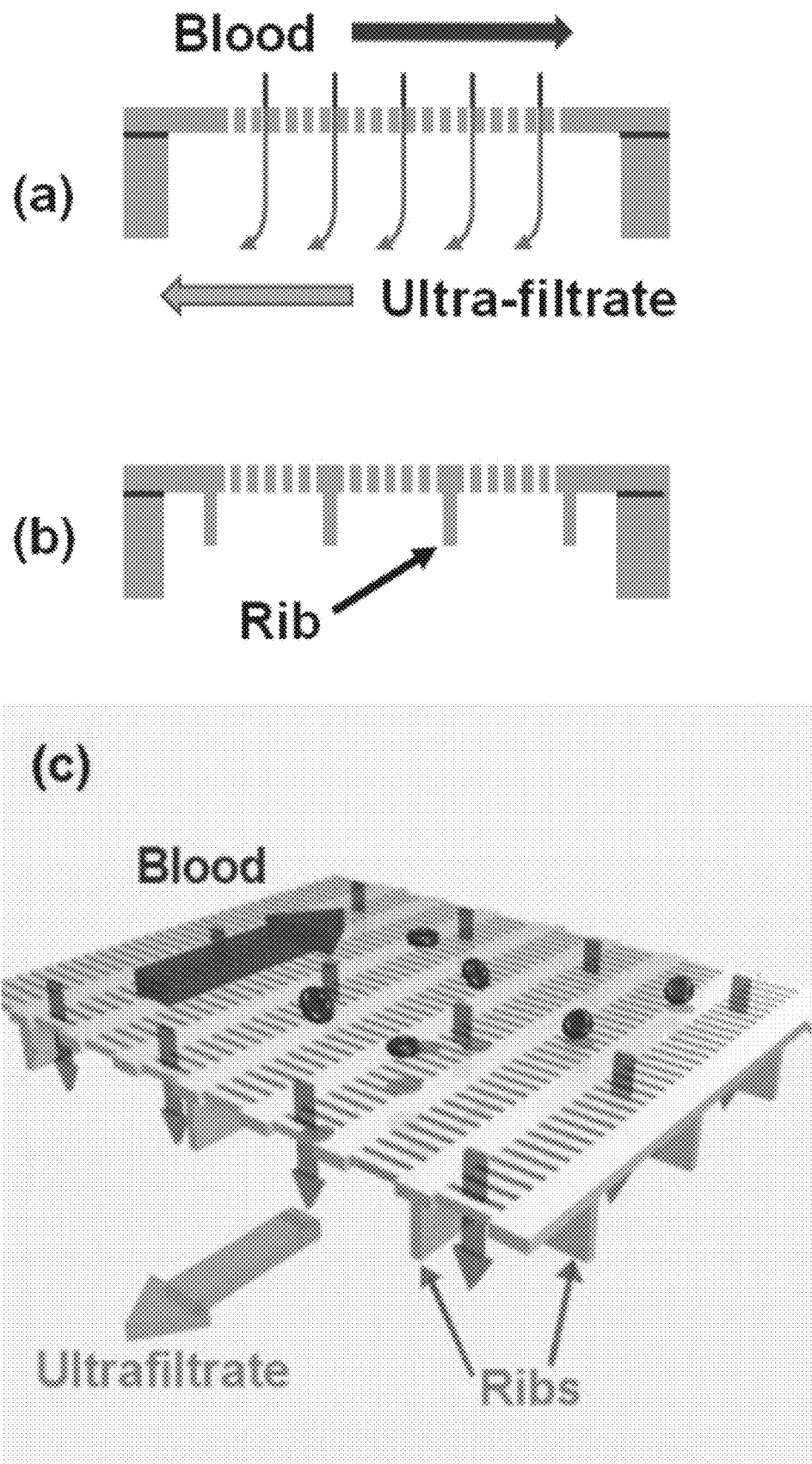
FIG. 1 depicts conceptual diagram of a flat membrane (a) and a ribbed membrane (b) and (c) a 3-dimensional (3D) rendition of orthogonal network of backside ribs.

All publications, patents and patent applications cited herein, whether supra or infra, are hereby incorporated by reference in their entireties.

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a membrane" includes a plurality of two or more such membranes, and the like. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

By "subject" or "individual" is meant any member of the subphylum Chordata, including, without limitation, humans and other primates, including non-human primates such as chimpanzees and other apes and monkey species; farm animals such as cattle, sheep, pigs, goats and horses; domestic mammals such as dogs and cats; birds; and laboratory animals, including rodents such as mice, rats and guinea pigs, and the like. The term does not denote a particular age. Thus, both adult and newborn individuals are intended to be covered.

The term "about" as used herein when referring to a measurable value such as a physical quantity, a temporal duration, and the like, is meant to encompass variations of ±20%, such as ±10%, such as ±5%, ±1%, including ±0.1% from the specified value, as such variations are typical of measurements characterizing the disclosed devices or appropriate to perform the disclosed methods.

As used herein "substantially", may be applied to modify any quantitative representation that could permissibly vary without resulting in a change in the basic function to which it is related. For example, substantially parallel may encompass structures that are slightly non-parallel to each other.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

"Biocompatible," as used herein, refers to a property of a material that allows for prolonged contact with a tissue in a subject without causing significant toxicity or significant damage.

"Planar" as used herein, may be applied to describe a three-dimensional shape of any object, where the length scale of two dimensions that are substantially perpendicular to each other (e.g., length and width) is longer than the length scale of a third dimension (e.g., thickness) that is substantially perpendicular to both of the other two dimensions. The length scale of one of the two longer dimensions may be similar to or different from the other longer dimension. Planar when used in the context of a surface refers to a flat surface as opposed to a surface that includes protrusions. A membrane layer as provided herein may include a first surface that is substantially planar, i.e., the length and width define a plane surface that is smooth as it does not include significant protrusions or depressions, and a second surface opposite the first surface that may be non-planar, e.g., having protrusions or ribs extending from the second surface which protrusions or ribs are separated by substantially smooth surface. The first surface of the membrane formed from the membrane layer has a plurality of nanopores extending between the first and second surface, where the nanopores are absent from the regions where the protrusions are present.

"Nanopore" as used herein, refers to a pore that penetrates a membrane from one side to another, where the pore has at least one lateral dimension (e.g., width and/or length, but not the height/thickness of the pore across the substrate) that is in the nanometer range, e.g., in the range of 1.0 nm to 1,000 nm.

As used herein, the term "polysilicon" refers to a polycrystalline form of silicon that is deposited as a thin film. It is used in microelectronics for transistors and wiring. In MEMS, polysilicon is usually used as structural material for devices.

"Pumpless" as used in reference to a blood circuit is meant to refer to the absence of a pump mechanism other than the pump mechanism (e.g., the heart) that drives blood flow through the circulatory system of an individual.

As used herein, the term "filtration" refers to a process of separating particulate matter from a fluid, such as a liquid, by passing the fluid carrier through a medium that will not pass the particulates.

As used herein, the term "individual" refers to any animal, such as a mammal like a dog, cat, livestock (e.g., pig), non-human primate, and including a human. The individual may be a patient with a compromised kidney function and/or in need of dialysis, compromised heart function, and/or compromised liver function.

As used herein, the term "dialysis" refers to a form of filtration, or a process of selective diffusion through a membrane; it is typically used to separate low-molecular weight solutes that diffuse through the membrane from the colloidal and high-molecular weight solutes which do not. In some embodiments, a feed of fluid is passed over a semi-permeable membrane, and a feed of dialysate is passed over the other side of that membrane; the membrane is wetted by one or both fluids, and then there is diffusive transport of solutes between the fluids. The composition of one fluid, the dialysate, may be used to deplete the composition of the other fluid, the feed fluid, of some molecule or molecules.

As used herein, the term "ultrafiltration" refers to subjecting a fluid to filtration under pressure, where the filtered material is very small; typically, the fluid includes colloidal, dissolved solutes or very fine solid materials, and the filter is a microporous, nanoporous, or a semi-permeable medium. A typical medium is a membrane. The fluid to be filtered is referred to as the "feed fluid." During ultrafiltration, the feed fluid is separated into a "permeate" or "filtrate" or "ultrafiltrate," which has been filtered through the filter, and a "retentate," which is that part of the feed fluid which did not get filtered through the medium, or which is retained within the membrane. Ultrafiltration does not require a dialysate be passed over the other side of the membrane.

As used herein, the term "dialysate" is used to refer to the fluid into which low-molecular weight solutes diffuse through a membrane from another fluid (typically, the feed fluid) initially containing these solutes.

Before describing the present invention in detail, it is to be understood that this invention is not limited to particular materials or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

DETAILED DESCRIPTION

The present disclosure provides methods for fabricating membranes for in vivo filtration, where the membranes include protrusions or ribs extending from the backside of the membrane. The protrusion or ribs are portions of the membrane where the membrane is thicker and hence more mechanically robust as compared to a membrane of a uniform thickness.

A method for generating a membrane for in vivo filtration of blood is disclosed. The method may include forming grooves in a grid pattern on a first surface of a substrate; depositing a membrane material into the grooves and over the first surface of the substrate thereby forming a membrane layer comprising a substantially planar front side and a non-planar backside comprising ribs corresponding to the grooves; forming a cavity in a second surface of the substrate by removing a portion of the substrate, wherein the second surface is opposite the first surface, wherein the cavity exposes the backside of the membrane; and forming a plurality of pores in the membrane layer thereby producing a membrane comprising a planar front side, a plurality of pores, and a non-planar backside comprising ribs.

In certain embodiments, forming grooves in a grid pattern on the first surface of the substrate may include etching to remove portions of the substrate from the front side of the substrate. In certain embodiments, etching may be wet etching using a wet etchant such as, potassium hydroxide, tetramethylammonium, buffered hydrofluoric acid, EDP, etc. The determination of when to stop the etch process can be based on a desired depth of the grooves. The wet etch may be isotropic or orientation selective, i.e., anisotropic. Etching may produce grooves with straight sides or sloped sides. In other embodiments, etchants can be used that are more anisotropic and produce little or no sloping of the groove walls. Alternatively, a reactive ion etching may be performed.

The substrate may act as a support section for the membrane. For example, the second surface of the membrane may be exposed in the cavity in the substrate, wherein the remainder of the substrate defining the boundary of the cavity provide mechanical support to the membrane. However, different from the membranes and associated devices disclosed in U.S. Patent Application Pub. No. US 2015-0090661 A1, the membrane exposed within the cavity in the substrate is not supported by portions of substrate remaining under the membrane in the cavity. Rather, the exposed region of the membrane in each cavity is supported by presence of protrusions or ribs in the lower surface of the membrane, where the protrusions or ribs are made from the same material as the membrane.

The substrate may be made of any inert material that does not foul when exposed to aqueous fluids, such as, ultrafiltrate filtering across the membrane. In some cases, a semiconductor material such as silicon wafer may be used for forming the substrate. The silicon wafer that may have a variety of crystal orientations including a [100] plane orientation as listed by the Miller indices. In other cases, the substrate may be germanium, Group IV elements of the periodic table, III-V compounds including gallium arsenide, II-IV compounds including zinc tellurium, p and n doped compounds, etc.

The substrate may be substantially planar and may have circular or straight edges. The substrate may be cut into rectangular pieces or circular pieces. The thickness of the substrate may be less than about 400 µm, about 600 µm, about 700 µm, about 900 µm, etc. or more.

In certain embodiments, the grid pattern comprises an array of rectangles and the ribs define a periphery of the array of rectangles. In certain embodiments, the grid pattern comprises an array of squares and the ribs define a periphery of the array of squares.

In certain embodiments, the ribs have a substantially uniform thickness. In certain embodiments, the ribs have a tapered shape. In certain embodiments, the ribs have a height in the range of 1 µm-10 µm, e.g., 2 µm-8 µm or 2.5 µm-5 µm. In certain embodiments, the ribs have a width of 0.5 µm-5 µm, e.g., 1 µm-2.5 µm.

In certain embodiments, prior to depositing a membrane material in the grooves and over the first surface of the substrate to form a membrane layer comprising a substantially planar front side and a non-planar backside comprising ribs corresponding to the grooves, an intermediate layer may be formed on the substrate. The intermediate layer may be a protective layer, such as, a dielectric layer. In some cases, the intermediate layer may be formed by depositing an oxide or nitride layer over the substrate or may be grown on the substrate. The intermediate layer may be deposited by chemical vapor deposition (CVD) including low pressure CVD (LPCVD) and plasma enhanced CVD (PECVD), or by some other deposition means. In some cases, the intermediate layer may be grown with a thermal process, such as thermal oxidation. The intermediate layer may include a silicon nitride, silicon oxide, silicon oxynitride, silicon carbide, or some other layer of material including other dielectric materials and combinations. The thickness of the intermediate layer may be about 2 µm or less, e.g., 2 µm-0.1 µm, 1 µm-0.2 µm, 1 µm-0.5 µm, or 0.8 µm-0.5 µm.

The membrane may be formed with any number of materials that can be deposited or grown on a micro- or nano-thick scale. For example, the membrane may be made from membrane materials such as silicon, polysilicon, silicon carbide, ultra nanocrystalline diamond, diamond-like-carbon, silicon dioxide, SU-8, titanium, silica, silicon nitride, polytetrafluorethylene, polymethylmethacrylate, polystyrene, silicone, or various other materials. The membrane material may be deposited by the same or a different deposition means and may include LPCVD in one example. The thickness of the membrane layer may be less than 5 µm, e.g., 5 µm-0.5 µm, 4 µm-0.5 µm, 3 µm-0.5 µm, 2 µm-0.5 µm, 1 µm-0.5 µm, or 0.8 µm-0.4 µm.

Prior to forming a cavity in the backside of the substrate, a plurality of nanopores may be formed in the membrane layer by patterning and etching the front-side of the membrane layer. In some cases, pore structures may be formed with a sacrificial material that may be later removed to form pores through the membrane layer. The pore structure may be formed with an etching process, or other lithography process. The membrane layer may be patterned with a photoresist that may be performed via e-beam, deep ultraviolet lithography, or another patterning technique that can form patterning for creating structures as described herein. The resist pattern may be transferred via a reactive ion etch or wet etch process onto the membrane layer. Following the patterning, a sacrificial layer of material may be formed on or within the patterned membrane layer. The sacrificial layer may be an oxide grown via thermal oxidation that may be less than 20 nm thick. Alternatively, the layer may have a thickness of less than or about 15 nm, 10 nm, 7 nm, 5 nm, 3 nm, 1 nm, 5 angstroms, etc., or less. The layer of material may be conformal when grown, and thus the film may be formed via a more conformal process including high density plasma CVD (HDPCVD), or some other conformal deposition process. The layer may be silicon oxide, or any other material that can be subsequently removed from the membrane layer to create the membrane with pores.

The layer of sacrificial material may be selectively removed in certain areas with a subsequent photoresist patterning and etch. This may provide areas for anchoring a second membrane layer to the first membrane layer during a subsequent deposition. After removing the photoresist, a second membrane material may be deposited filling in the anchor cavities, as well as the areas around the sacrificial layer in and around the trenches formed in the first membrane material. This material may be the same or a different membrane material as previously described. For example, the second membrane material may also be polysilicon. The second membrane material layer may be planarized down at least to a level exposing the sacrificial material, and thereby forming the pore structure. The planarization may occur with any polishing or etching technique and can include a reactive ion etch in one example. In still another example, the anchors may be formed and filled subsequent to depositing the second membrane material and performing a planarization. The process may alternatively be performed by performing an additional lithography step followed by a direct etching, such as with a reactive ion etch, followed by a specific deposition for the anchor material.

The pores may also be more densely patterned by performing a series of patterning and deposition processes. For example, subsequent to the initial deposition of the membrane material, a secondary patterning step similar to that as described above may be performed. Once the secondary patterning has been performed, an additional protective layer may be deposited in a way as previously described. Following the formation of the additional protective layer, a subsequent layer of membrane material may be formed to provide the degree of pore spacing required. The repetitive processing may reduce the line and space pattern by 20% or more. Alternatively, the repetitive processing can reduce the line and space pattern by about 30% or more, about 40%, about 50%, about 55%, about 60%, about 65%, about 70%, about 75%, about 80%, about 85%, about 90%, etc., or more. By maintaining the protective material within the pores during fabrication, pore integrity may be maintained until a final release is performed.

A second protective layer may be applied over the membrane materials prior to backside etching of the substrate to form the cavity and expose the membrane. The second protective layer may include an oxide, nitride, or another compound depending on the etching technique subsequently performed. For example, a nitride layer may be deposited if a potassium hydroxide etch is performed, and an oxide layer may be deposited if the subsequent etch includes a chemical selective to nitrogen, such as tetramethylammonium hydroxide.

In some embodiments, the cavity is substantially rectangular. In some embodiments, a plurality of cavities in a grid pattern are formed. In some embodiments, the cavities have a length in the range of 250 µm-1000 µm and a width of 25 µm-100 µm, e.g., length of 500 µm-1000 µm and a width of 25 µm-100 µm or a length of 25 µm-50 µm and a width of 10 µm-25 µm. The area of the backside of the membrane exposed by the cavity may be in the range of 10,000-50,000 µm$^2$. In some embodiments, the backside of the membrane exposed by the cavity is substantially rectangular and has a length of about 500 µm-1000 µm and a width of about 25 µm-100 µm. In some embodiments, the backside of the membrane exposed by the cavity comprises about 10-30 rectangular ribs. In some embodiments, the ribs are arrayed at a periodicity of one rib after every 25 µm-50 µm distance along the length of the exposed membrane. In some embodiments, the ribs are arrayed at a periodicity of one rib after every 10 µm-25 µm distance along the width of the exposed membrane. In some embodiments, the long length of the rectangular ribs is substantially parallel to the long length of the cavity. In some embodiments, the thickness of membrane in regions between the ribs is in the range of 500 nm-1 µm. In some embodiments, the thickness of membrane in regions between the ribs is in the range of 0.75 µm-1 µm.

The plurality of pores may be slit shaped pores. In some embodiments, the slit shaped pores have a length of up to 3 µm and a width of up to 0.1 µm, e.g., a length of up to 2 µm and a width of up to 50 nm or a length of 1 µm-3 µm and a width of 10 nm-100 nm. In some embodiments, the longer side of the pore is perpendicular to the longer side of the ribs. In some embodiments, the longer side of the pore is parallel to the longer side of the ribs.

Also provided herein are filtration devices comprising filtration membranes. In certain aspects, the filtration membranes may be integrated into a housing comprising pre-fabricated partial channels which in conjunction with the filtration membranes form flow path for blood flowing through the filtration device. The filtration membranes may be inserted into the housing comprising the pre-fabricated partial channels individually. Alternatively, a filtration membrane cassette formed by bonding filtration membranes in a spaced apart manner may be inserted into the housing and the cassette attached to the openings of the partial channels.

Figure 10:
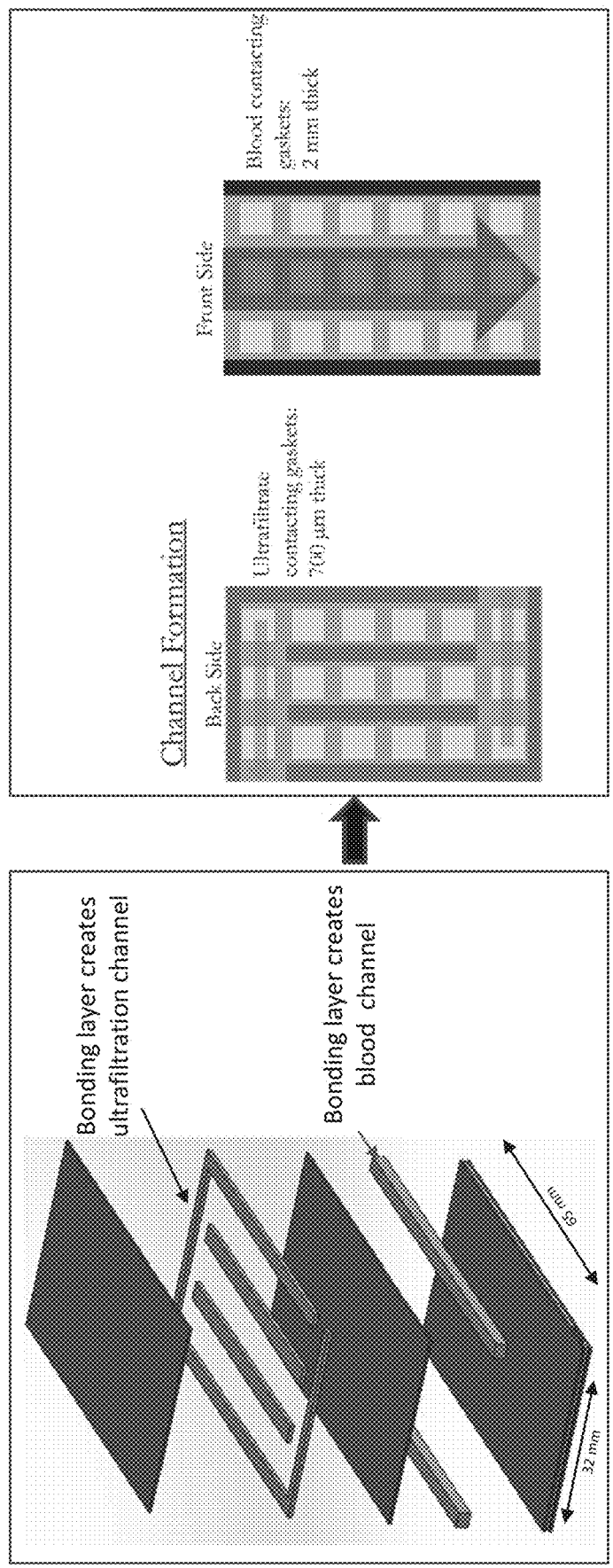
FIG. 10. Exploded view showing flow paths for ultrafiltrate and blood created between parallel silicone nanopore membranes.

In the embodiment depicted in FIG. 10, filtration membranes are bonded together in a stacked configuration. As noted herein, the membranes may be inserted one at a time into the housing and bonded or they may be pre-bonded to generate a filtration membrane cassette prior to insertion into the housing comprising the partial channels. FIG. 10 depicts the flow paths provided between filtration membranes for flow of blood alternating with flow paths provided between filtration membranes for flow of ultrafiltrate or dialysate. For forming a flow path for blood, filtration membranes may be positioned in a spaced apart manner using spacers disposed along the long edges of the membranes. The height of the spacer which defines the height of the channel for blood flow may range from 0.5 mm-5 mm, e.g., 0.8 mm-4 mm, 0.8 mm-2.5 mm, 1 mm-2.5 mm, or 1.5 mm-2.5 mm. The spacers may have a width that provides a surface for adhering two membranes such that the adherence between two membranes is sufficient to withstand blood pressure higher than 300 mmHg. In certain aspects, the width of the spacer may range from 2 mm-5 mm, e.g., 2.25 mm-3.75 mm, 2.25 mm-3.5 mm, 2.25 mm-3.25 mm, 2.25 mm-3 mm, or 2.5 mm-3 mm. The spacers may be positioned on the membranes at or close to the edges of the membranes to maximize the width of the flow path defined between the spacers and membranes. In certain aspects, the spacers may be spaced apart by a width of 20 mm-100 mm, e.g., 20 mm-80 mm, 20 mm-70 mm, 20 mm-50 mm, 20 mm-40 mm, or 20 mm-30 mm.

For forming a flow path for ultrafiltrate or dialysate, filtration membranes may be positioned in a spaced apart manner using spacers disposed discontinuously along the periphery of the membranes. Optionally, there may be additional spacers disposed between interior surfaces of the membranes. In certain aspects, there may be one-four additional spacers disposed between two membranes along an interior surface of the membranes. In certain aspects, the spacers positioned along the long edges between membranes may not extend to the short edge to provide an opening at the long edge defining an outlet for ultrafiltrate or an inlet or outlet for dialysate. FIG. 10 depicts such a configuration. In certain aspects, the spacers positioned along the short edges between membranes may not extend to the long edge to provide an opening along the short edge defining an outlet for ultrafiltrate or an inlet or outlet for dialysate. A flow path for ultrafiltrate may include at least one opening for exit of ultrafiltrate generated from filtration across the membranes. In certain aspects, flow path for ultrafiltrate may include at least two, three, or four openings for exit of ultrafiltrate generated from filtration across the membranes. In certain aspects, flow path for ultrafiltrate may include two openings for exit of ultrafiltrate generated from filtration across the membranes. The spacers positioned along the edges between the filtration membranes may be configured to provide the desired number of openings. The height of the spacer which defines the height of the channel for ultrafiltrate or dialysate flow may range from 0.1 mm-1 mm, e.g., 0.25 mm-1 mm, 0.5 mm-1 mm, or 0.5 mm-0.75 mm. The spacers may have a width that provides a surface sufficient for adhering two membranes. In certain aspects, the width of the spacer may range from 2.25 mm-4 mm, e.g., 2.25 mm-3.75 mm, 2.25 mm-3.5 mm, 2.25 mm-3.25 mm, 2.25 mm-3 mm, or 2.5 mm-3 mm. In certain aspects, positioned in the interior between two membranes may be spaced apart by a width of 5 mm-10 mm from the edges of the spacers positioned along the periphery of the membranes and from each other.

The spacers may be made from any suitable material, e.g., a biocompatible polymeric material, such as, but not limited to, silicone, polysiloxane, poliglecaprone, polydioxanone, polyglactin, caprolactone, polyorthoester, polyethylene glycol, poly terephthalate, tyrosine, poly(ester amide), polyisobutylene, poly(ethylene terephthalate), polytetrafluoroethylene, polyurethane, polystyrene, polyamide, polyimide, bisphenol-alpha-glycidyl methacrylate, triethyleneglycol dimethacrylate, hydroxyethyl methacrylate, poly-p-chloroxylylene, phenolic resins, and the like. The spacers may be adhered to surfaces of the membranes using any suitable non-toxic adhesive. In certain aspects, the spacers may define two side walls of the flow paths, which flow paths are connected to an inlet and an outlet for entry and exit of blood in the flow path. The membrane used for filtration may be a biocompatible membrane used in the field of dialysis and/or ultrafiltration, such as, silicone membrane, silicon nanopore membrane (SNM), silicon nitride, silica, atomically thin membrane such as graphene, silicon, silicene, molybdenum disulfide ($MoS_2$), etc., or a combination thereof, or a polymer.

In certain embodiments, the membrane may include a plurality of nanopores having a circular or slit shaped opening with a diameter or width, respectively, of 1 nm-500 nm, e.g., 1 nm-90 nm, 2 nm-50 nm, 3 nm-40 nm, 4 nm-50 nm, 4 nm-40 nm, 5 nm-50 nm, 5 nm-20 nm, 4 nm-20 nm, 7 nm-100 nm, 12 nm-20 nm, or 5 nm-10 nm. In certain embodiments, the membrane comprises a plurality of micropores having a circular or slit shaped opening with a diameter or width, respectively, in the range of 0.1 µm-5 µm, e.g., 0.1 µm-3 µm, 0.1 µm-0.5 µm, 0.5 µm-1 µm, 1 µm-1.5 µm, 1.5 µm-2 µm, 0.1 µm-1 µm, 0.1 µm-0.8 µm, 0.2 µm-0.7 µm, 0.2 µm-0.6 µm, 0.2 µm-0.5 µm. In certain embodiments, the plurality of pores are slit shaped and have a width as listed herein and have a length in the range of 1 µm-10 µm, e.g., 2 µm-3 µm, 3 µm-4 µm, 4 µm-5 µm, 5 µm-6 µm, 6 µm-7 µm, 7 µm-8 µm, 8 µm-9 µm, or 9 µm-10 µm. In certain cases, the slit shaped, i.e., rectangular pores have a depth of 100-1000 nm, a width of 3 nm-50 nm and a length of 1 micron-5 micron, e.g., a width×length×depth of 5 nm-50 nm×1 micron-2 micron×200 nm-500 nm. The depth of the pores may be defined by the thickness of the membrane which may be in the range of 0.1 micron-1000 micron.

FIG. 10 depicts stacking of filtration membranes for creating flow paths for blood and ultrafiltrate. The L-shaped spacers placed along the edges between two membranes provide a discontinuous sealing between the two membranes, thereby defining two openings along the long edges of the channel defined by the membranes and the spacers. Two additional spacers are included in the interior of the defined channel Thus, the ultrafiltrate/dialysate channel is defined between a second surface of a first membrane and a first surface of a second membrane which first and second membranes are positioned in a spaced apart manner by the spacers. The openings are connected to a channel in the housing, where the channel is configured to collect ultrafiltrate from each of the flow paths defined between the stacked membranes. The channel may be a circular or rectangular channel that extends from the first ultrafiltrate flow path defined between a first and second membrane to the last ultrafiltrate flow path defined between a penultimate and ultimate membrane in the stacked configuration of membranes. The second surface of the second membrane and the first surface of the third membrane are positioned in a spaced apart manner by spacers disposed along the long edges between the second surface of the second membrane and the first surface of the third membrane. These spacers extend from one short edge to the opposite short edge of the membranes.

The stacked membranes may form filtration regions connecting turn around sections of a serpentine blood conduit as described in International Application No. PCT/US17/30597, which is incorporated by reference herein. As described therein, the serpentine blood conduit may include a circular inlet configured for connection to a blood vessel of an individual; and a transition section in which lumen of the inlet transitions from having a circular cross-section to having a substantially rectangular cross-section which rectangular cross section is connected to a stacked membrane pair of a membrane cassette, the stacked membrane pair defining a blood flow path, the blood flow path connected to a second region of the serpentine conduit, where the second region includes a U-shaped turn and followed by connection to another stacked membrane pair of the membrane cassette. In certain aspects, the plurality of flow paths in the filtration regions of the hemofiltration device are substantially rectangular (e.g., with a length longer than width) and are stacked in a parallel configuration. In certain aspects, the serpentine conduit includes a circular outlet configured for connection to a blood vessel of an individual and the conduit transitions from a rectangular cross section to a circular cross section to form the circular outlet.

In certain aspects, the circular inlet, regions containing U-shaped turns, and the circular outlet may be preformed in a housing of the hemofilter and may be connected to a membrane cassette to provide a plurality of blood flow paths. In certain aspects, the housing may also include one or more preformed channels configured to connect to the ultrafiltrate/dialysate flow paths alternating with the blood flow paths.

In certain aspects, each of the plurality of blood flow paths in the filtration regions has a length of 10 mm-200 mm, e.g., 40 mm-100 mm. In certain embodiments, each of the plurality of blood flow paths in the filtration regions has a width of 5 mm-100 mm, e.g., 10 mm-40 mm. In certain embodiments, each of the plurality of blood flow paths in the filtration regions has a height of 0.5 mm-2.5 mm.

Figure 11:
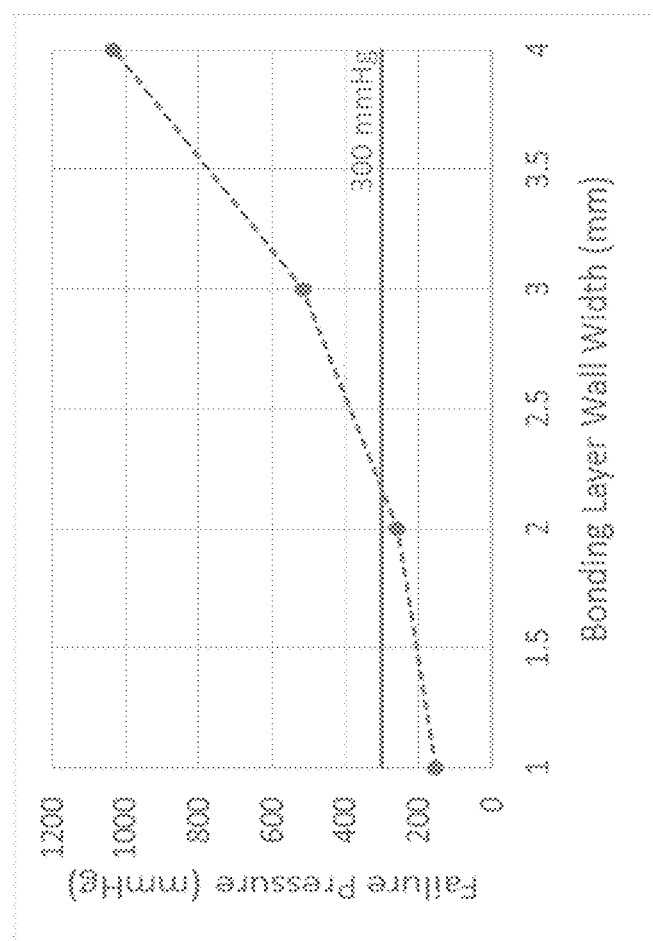
FIG. 11 illustrates failure pressure for indicated bonding layer wall widths.
Figure 11:
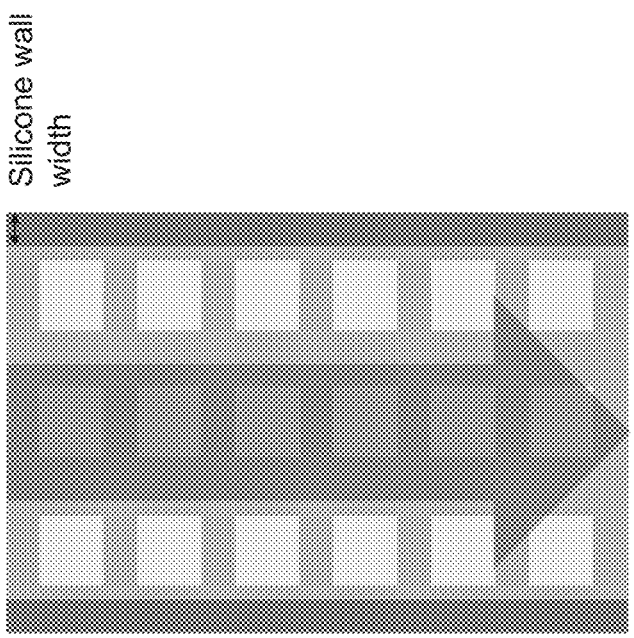

FIG. 11 shows results from testing of bond strength provided by varying widths of a silicone spacer. Pressure failure followed an exponential curve.

Figure 12:
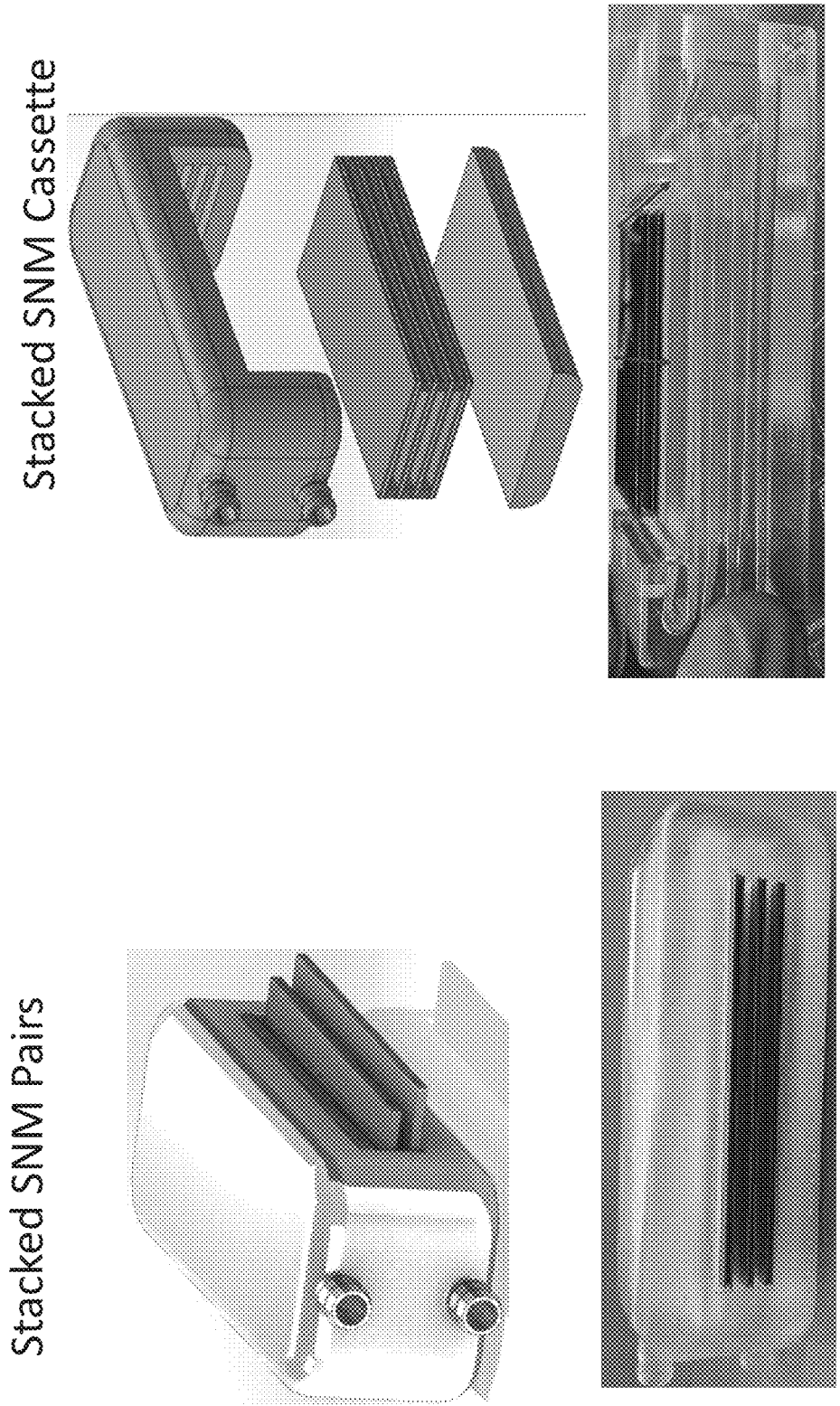
FIG. 12 illustrates hemofilters constructed from stacked silicon nanomembrane (SNM) pairs and from stacked SNM cassette.
Figure 13:
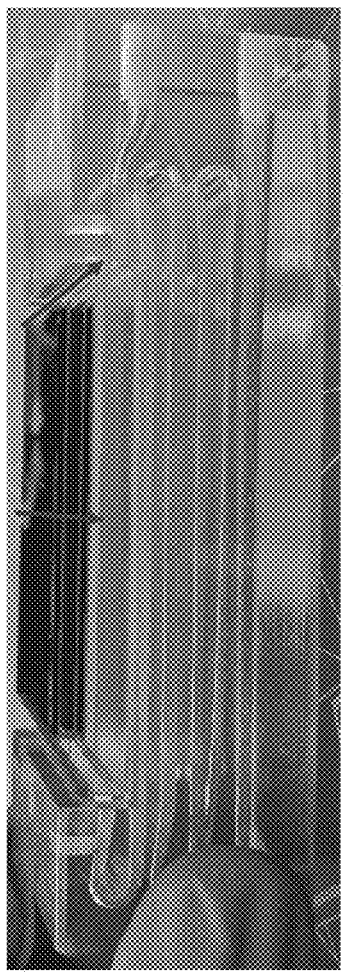
FIG. 13 illustrates hemofilter constructed from single SNM cassette.
Figure 13:
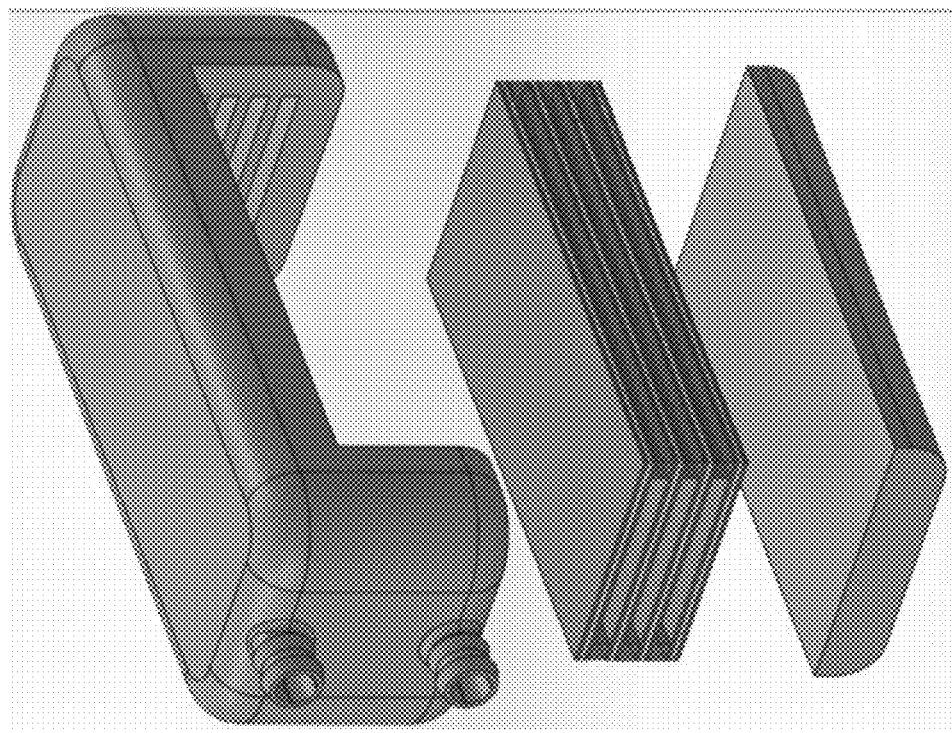
Figure 14:
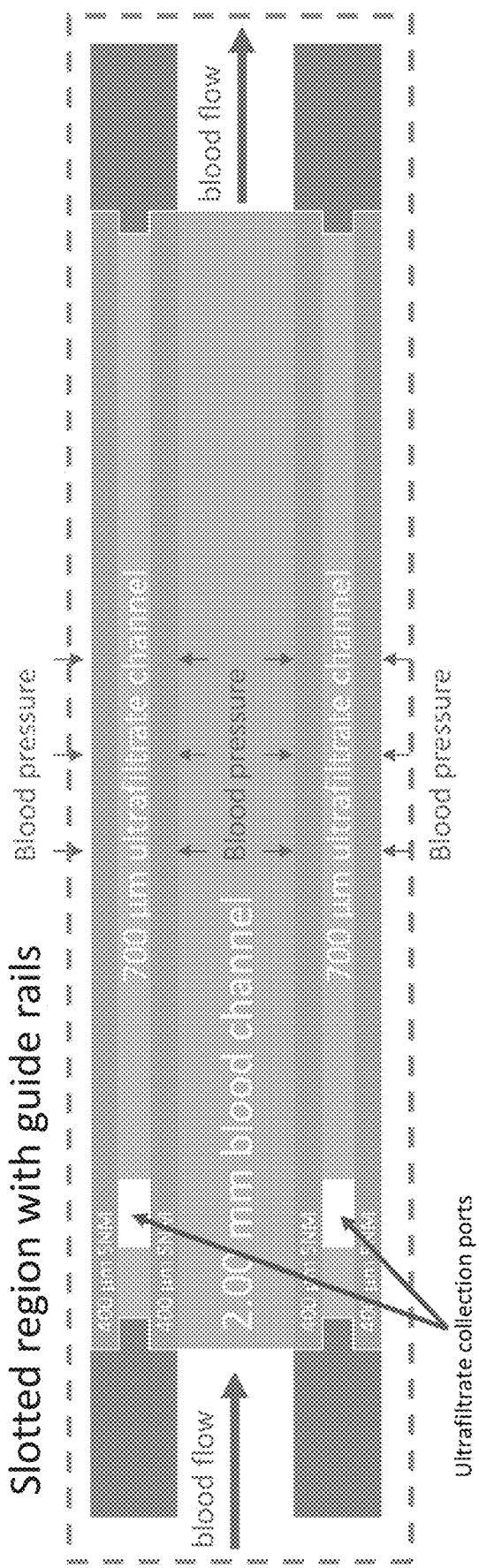
FIG. 14. Side view showing alternating parallel arrangement of blood and ultrafiltrate flow paths.
Figure 15:
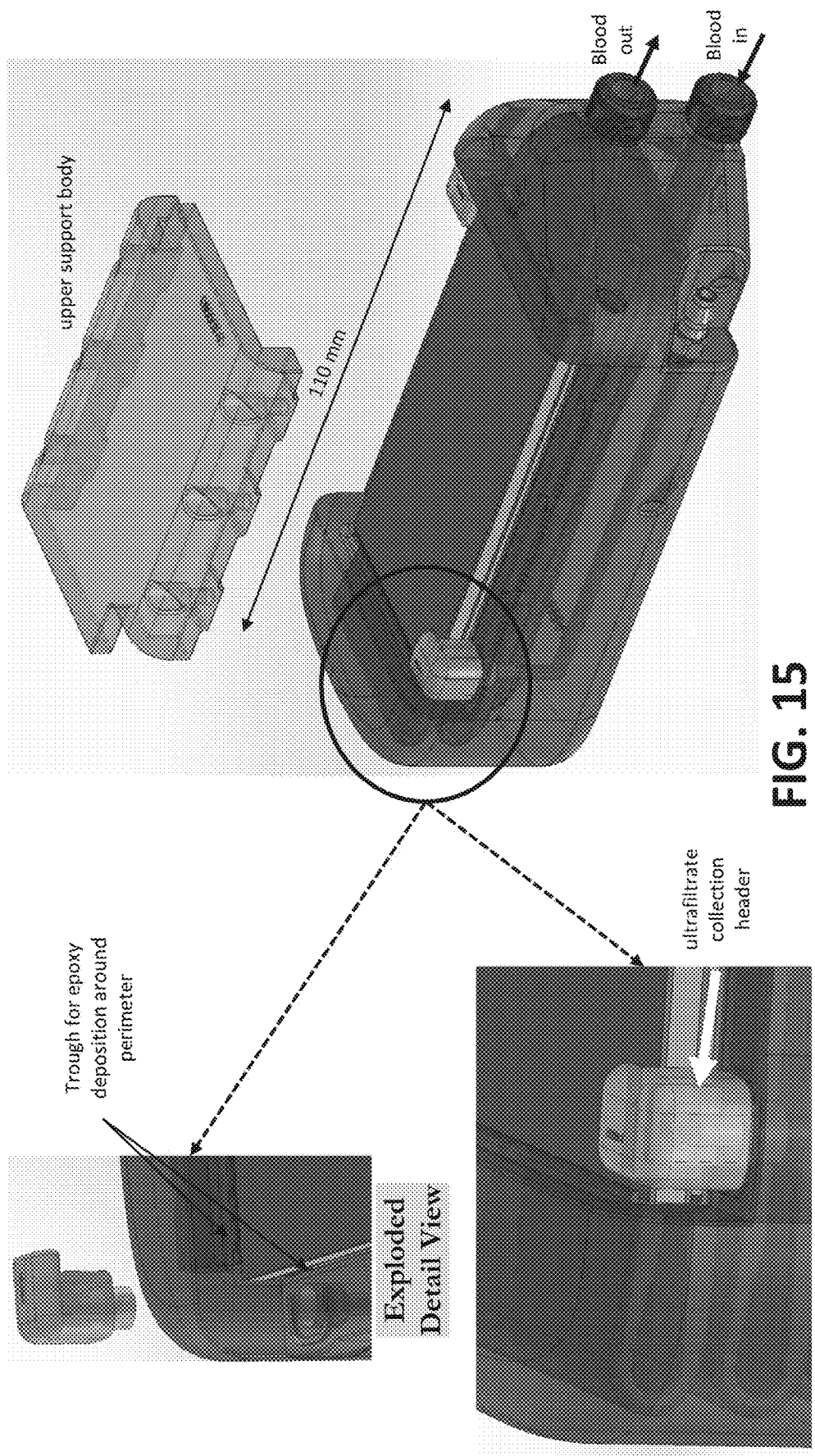
FIG. 15. Rendering of prototype assembly including exploded view of upper support plate.
Figure 16:
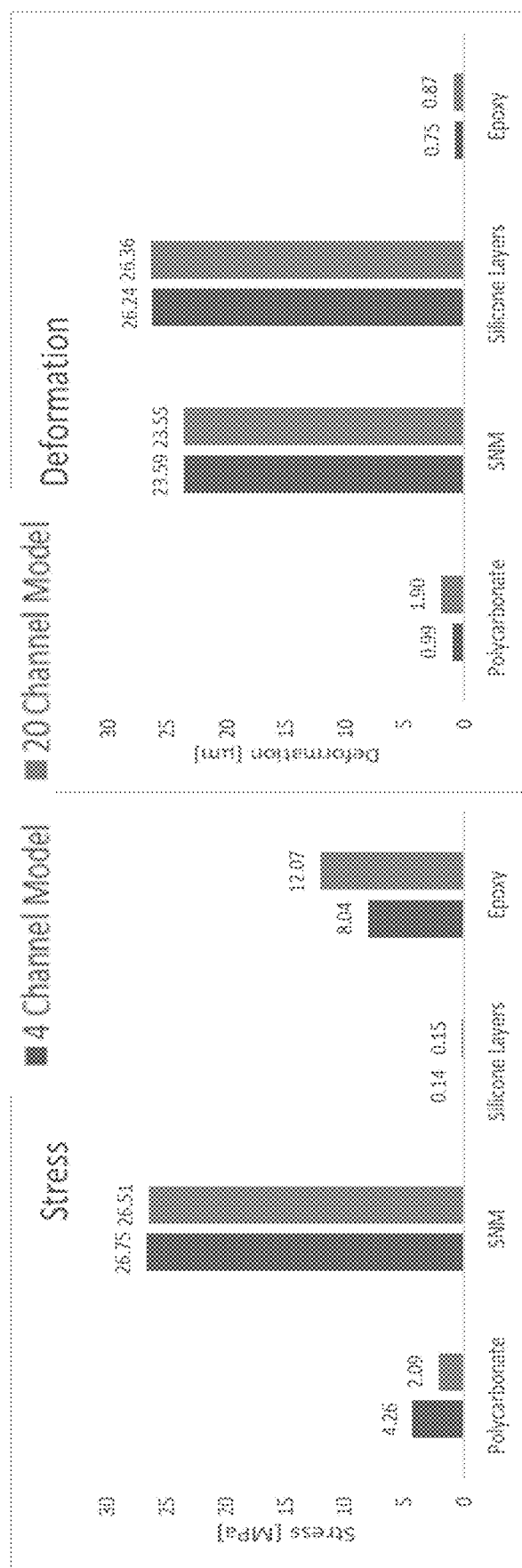
FIG. 16. Comparison of mechanical response of scaled down model (4-channel hemofilter device) and clinical-scale device (20-channel hemofilter device).
Figure 17:
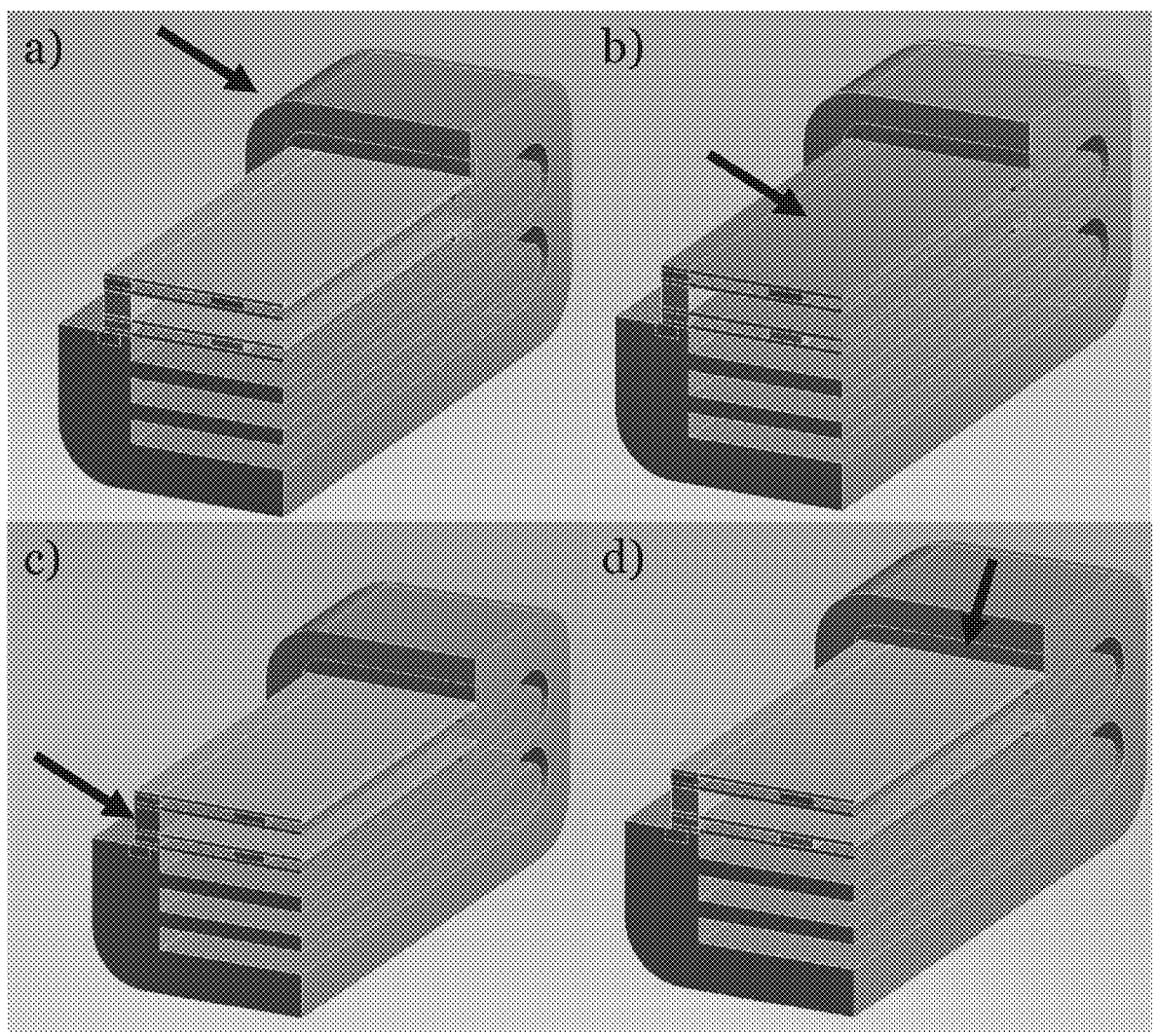
FIG. 17. Model geometry of 4-channel hemofilter device.
Figure 18:
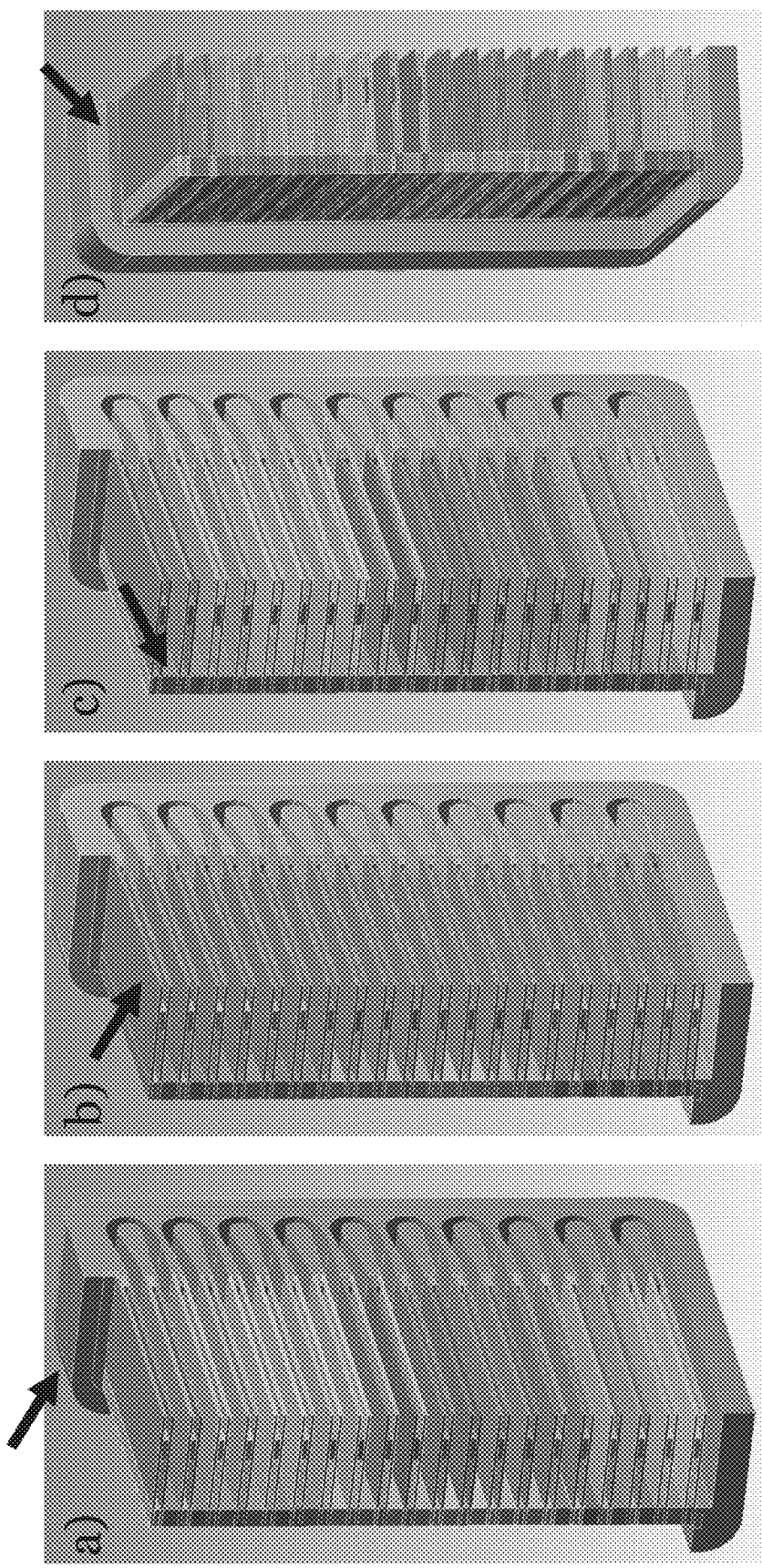
FIG. 18. Model geometry of clinical-scale, 20-channel hemofilter device.

FIG. 12 shows fabrication of a filtration device by inserting stacked pairs of membranes or a cassette of stacked membranes.

In certain aspects, the in vivo infiltration device, such as, a bioartificial kidney is dimensioned to fit in a body cavity of a subject. The in vivo infiltration device may be rectangular or cylindrical in shape. In certain case, the in vivo infiltration device may have a surface area of 50 $cm^2$ or less, such as 10-30 $cm^2$, 10-25 $cm^2$, 15-25 $cm^2$, 20-25 $cm^2$, 15-30 $cm^2$. In certain cases, the bioartificial kidney may be rectangular and have a length of 3 cm-10 cm, a width of 1 cm-6 cm, and a height of 0.3 cm-2 cm, such as dimension (length×width×height) of 3 cm×1 cm×0.5 cm to 6 cm×4 cm×1 cm, e.g., 3 cm×1 cm×0.5 cm, 5 cm×2 cm×1 cm, or 6 cm×4 cm×1 cm. In certain embodiments, the overall dimension of the hemofilter, specifically the filtration section of the hemofilter, such as those depicted in the figures provided herein may range from 45 mm-100 mm in height, 80-150 mm in length, and a width of 10-30 mm, such as, height×length×width of 45-80 mm×90-130 mm×10-30 mm, respectively.

Any material suitable housing material may be used to form the hemofilters provided herein. In some embodiments, the housing may be fabricated, in part, from medical grade plastic, metals, such as, titanium, stainless steel, etc.

EXAMPLES

Below are examples of specific embodiments for carrying out the present invention. The examples are offered for illustrative purposes only and are not intended to limit the scope of the present invention in any way.

Efforts have been made to ensure accuracy with respect to numbers used (e.g., amounts, temperatures, etc.), but some experimental error and deviation should, of course, be allowed for.

Example 1: Variable Thickness Membrane

We have designed, fabricated, and tested nanoporous membranes with improved robustness and performance for the implantable bio-artificial kidney (iBAK). By superimposing a network of thicker "ribs" onto a thin membrane, we have shown that it is possible to achieve mechanically robust membranes and high filtration rates at the same time.

The "implantable bio-artificial kidney" is a long-term project at UCSF [1] aimed at eliminating the need for dialysis or kidney transplants for end-stage renal disease (i.e. kidney failure) which affects more than 650,000 patients in the US alone with treatment costs exceeding $35 billion per year.

One critical MEMS component of the iBAK is the filter unit, in which polysilicon membranes with nanoscale slit pores are used to mimic the kidney's filtering function in extracting creatinine and other harmful substances from blood [1]. The pore width (typically 5-30 nm wide) is set such that "useful" components (e.g. red/white blood cells) remain in the blood while "unwanted" components pass through into the ultrafiltrate due to the difference in pressure between the two sides.

We have previously developed a reliable process for fabricating such membranes with highly uniform and precisely tunable pore size [2]. To match the mass-transfer throughput of dialysis, however, another order-of-magnitude improvement is required: for example, by (i) implementing parallelism on the system level (e.g. multiple chips); (ii) increasing pore density at the chip level (advanced lithography or nano-imprint); and (iii) reducing flow-path resistance of the pores (e.g. thinner mem-brans). This disclosure describes option (iii): making membranes thinner without sacrificing mechanical integrity.

While thinning a membrane is desirable to minimize flow-path resistance, eventually the membrane becomes too fragile to withstand typical blood pressures. This is clearly unacceptable in implantable medical devices where long-term reliability is paramount. Therefore, we have designed a variable thickness membrane that includes a "thin" active porous area supported by a scaffolding of "thick" ribs criss-crossing the backside of the membrane surface to give it extra rigidity (see FIG. 1).

Ideally, the reinforcing elements should not take up too much active filter area. In addition, the rib protrusions should be on the back (filtrate) side of the chip to avoid impeding blood flow. This precludes an "additive" process wherein the rib material is deposited on top of an already-formed membrane layer.

Figure 2:
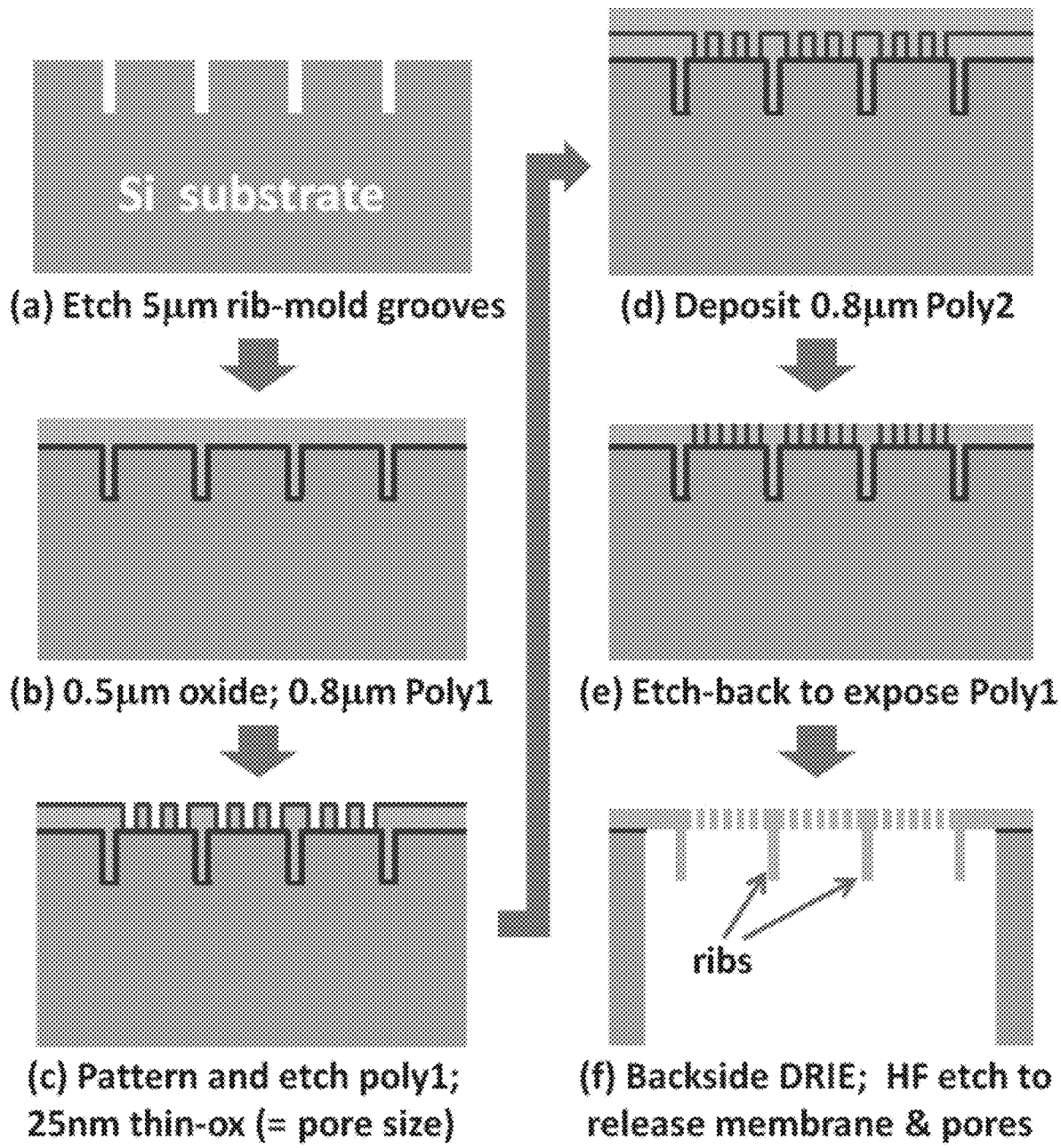
FIG. 2 depicts fabrication process flow for ribbed nanoporous polysilicon membranes.
Figure 3:
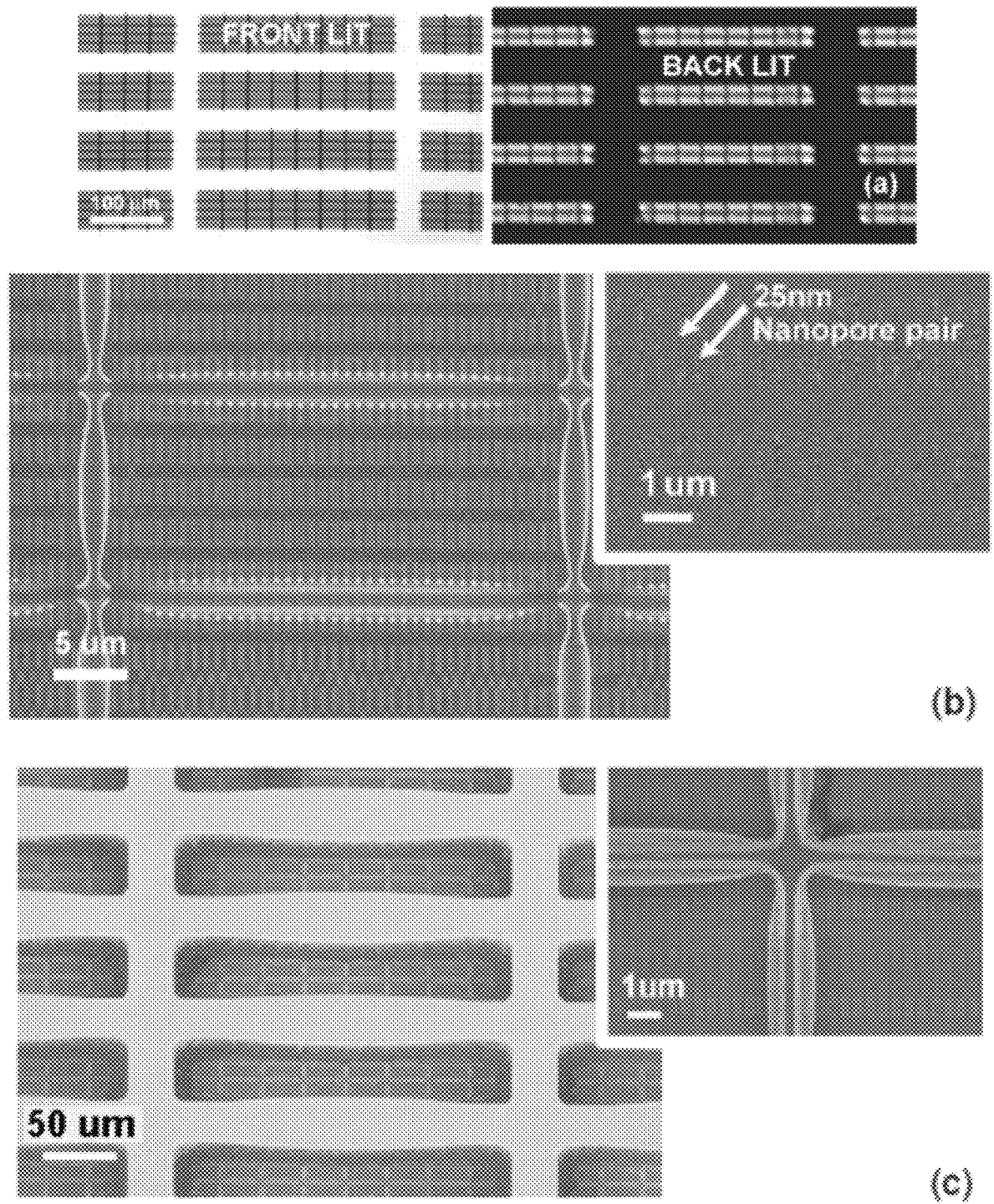
FIG. 3. (a) Optical image of ribbed membrane, (b) Top-view SEM (Inset shows details of the nanopore slits), and (c) Bottom-view SEM (Inset shows details of the ribs).

Accordingly, in this work we developed a new fabrication approach in which a grid of 1.5 µm-wide grooves (the "rib molds") are etched 2.5-5.0 µm deep into the surface of a Si substrate (FIG. 2a). A 0.5 µm thermal oxidation followed by a 0.8 µm poly-silicon deposition effectively fills up the grooves (forming the eventual ribs) and re-planarizes the surface. We then revert to the original process detailed in [3] (FIGS. 2c-2f). The finished device is shown in FIG. 3.

Figure 4:
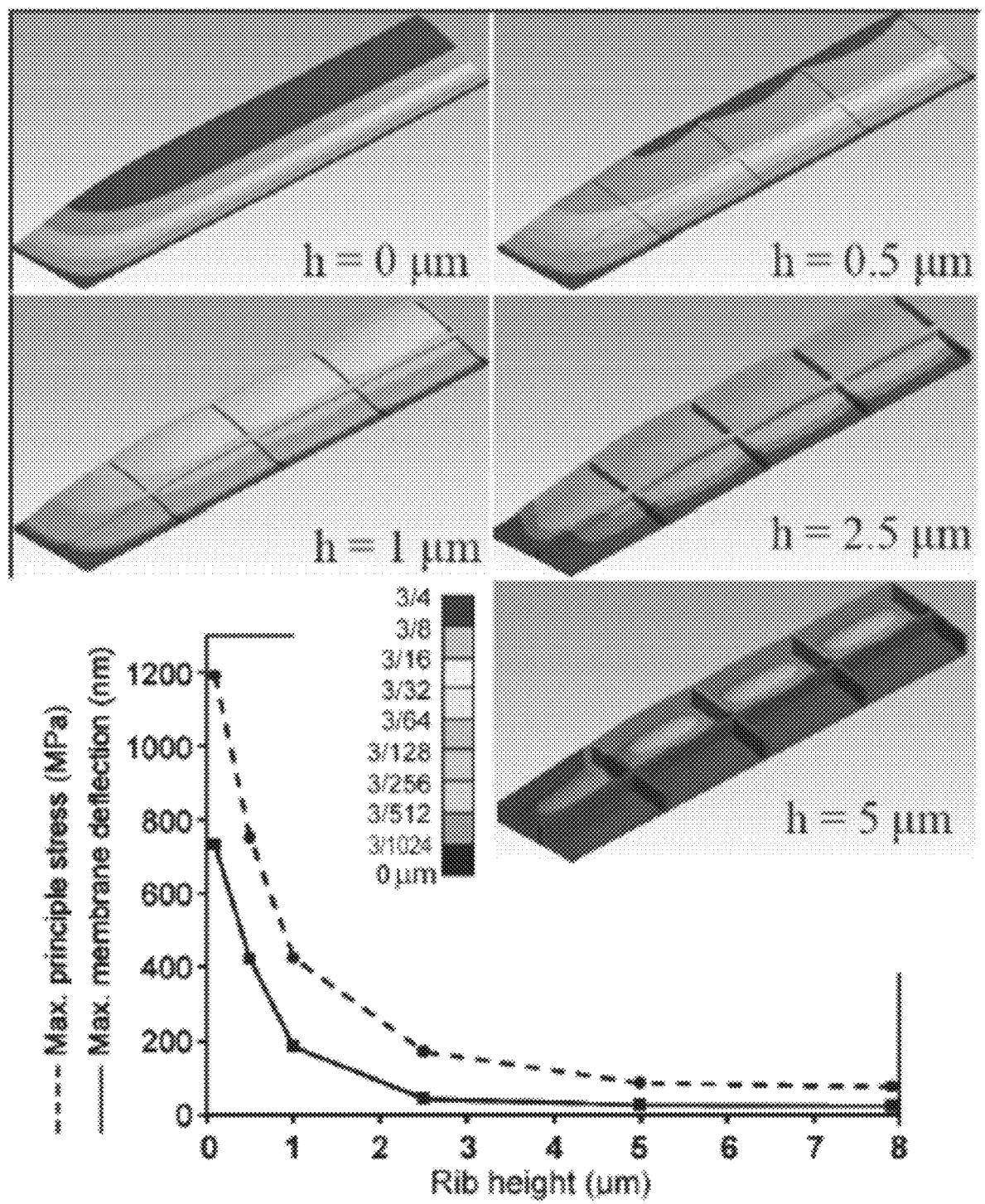
FIG. 4. Simulated membrane deflection and peak stress vs. rib height h for 300 mm Hg pressure. A logarithmic color scale is used to span the range of all five cases. The graph shows that membrane deflection (solid line) and peak stress (dotted line) both decrease rapidly (i.e. membrane strength increases quickly) with h.
Figure 5:
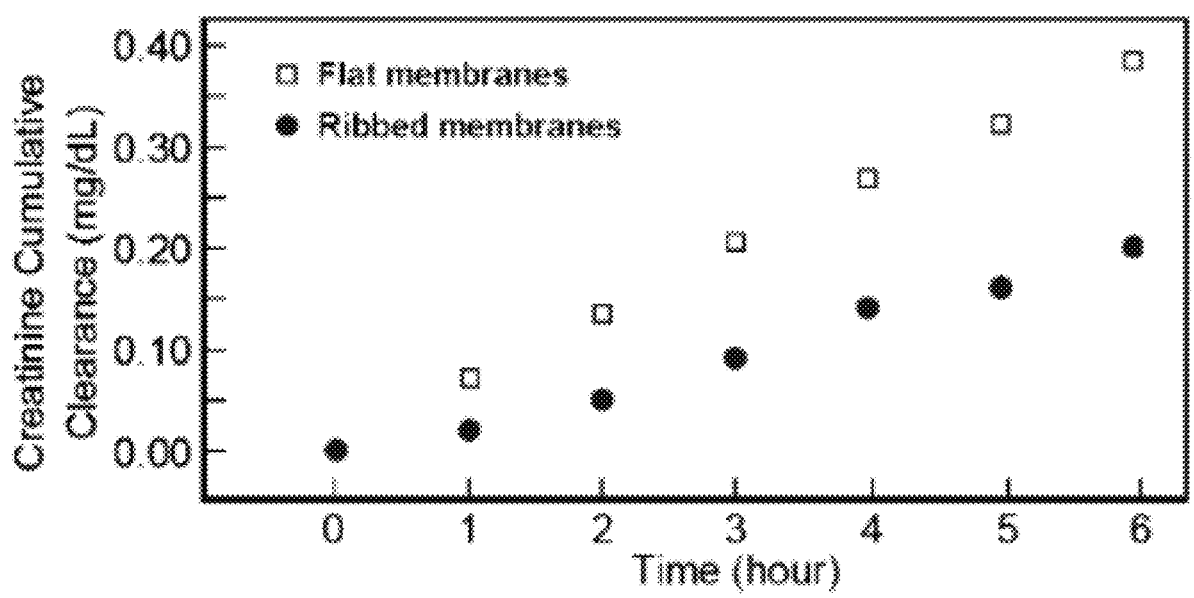
FIG. 5. Measured cumulative creatinine clearance for ribbed vs. flat membranes. The lower clearance for the former is partly due to a 13% reduction in pore area due to presence of ribs on the backside of the membranes.

To find a rib design that combines robustness with ease of fabrication, we performed finite-element modeling of membrane deflection and maximum stress vs. rib height h. We found that membrane strength increased quickly even with modest increases in h (FIG. 4). Accordingly, we made nanoporous membranes with 0 µm (i.e. flat), 2.5 µm and 5 µm-tall ribs and measured their hydraulic rupture threshold. Table 1 shows that the ribbed membranes performed 50-85% better than their flat counterparts, well worth the slight loss (13%) in active pore area. Both types of membranes were also subject to bio-filtration tests; FIG. 5 compares their creatinine clearance performance.

TABLE 1

Measured hydraulic rupture pressure for various designs

| (×1000 mm Hg) | Flat (no ribs) | 2.5 µm ribs | 5 µm ribs |
|---|---|---|---|
| Sample 1 | 1.03 | 2.22 | 2.69 |
| Sample 2 | 1.40 | 2.22 | 2.74 |
| Sample 3 | 1.91 | — | — |
| Average | 1.45 | 2.22 | 2.72 |

In conclusion, we have proven a new design and fabrication method that enables significantly thinner nanoporous membranes while preserving device robustness, thereby improving filtration efficiency on our way towards the ultimate goal of a fully implantable bio-artificial kidney—the "silicon kidney."

Example 2: Silicon Nanopore Membrane Based Implantable Hemodialyzer

Figure 6:
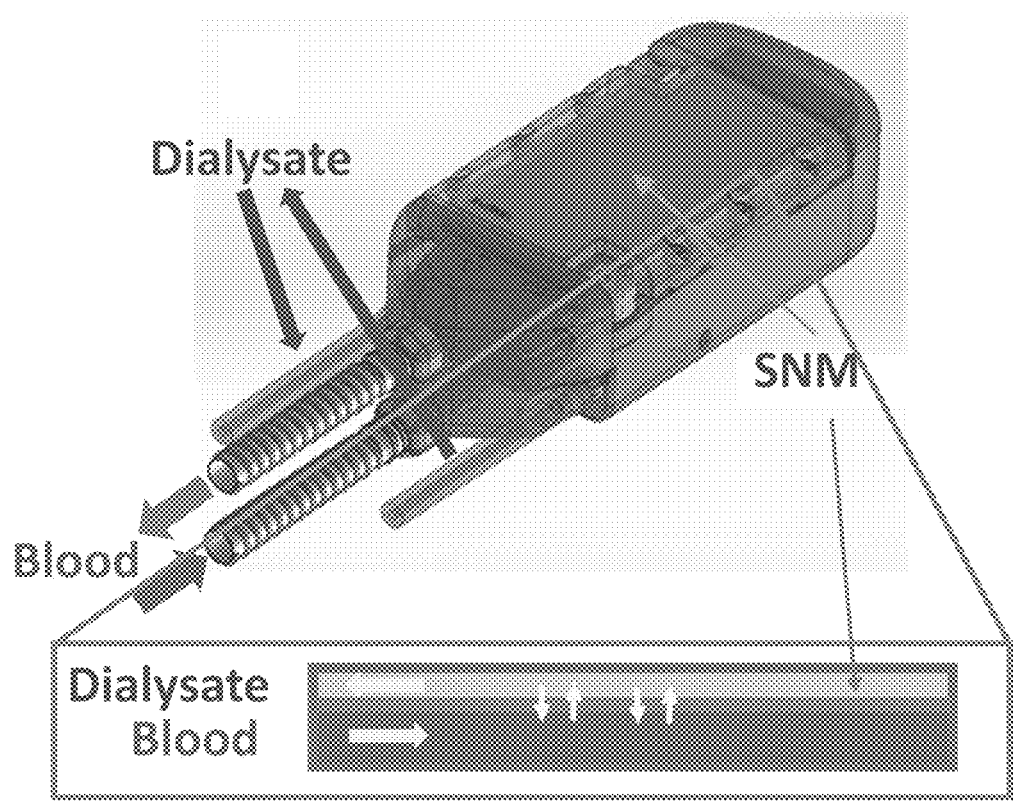
FIG. 6. Blood filtration device having parallel silicone nanopore membranes usable for perfusion-pressure blood filtering.

Blood filtration device comprising a parallel stacked membrane configuration with four filtration sections was implanted into a porcine subject. A schematic of the device is shown in FIG. 6. The flow of blood and dialysate is in opposite directions to enhance filtration of blood via the membrane.

Figure 7A:
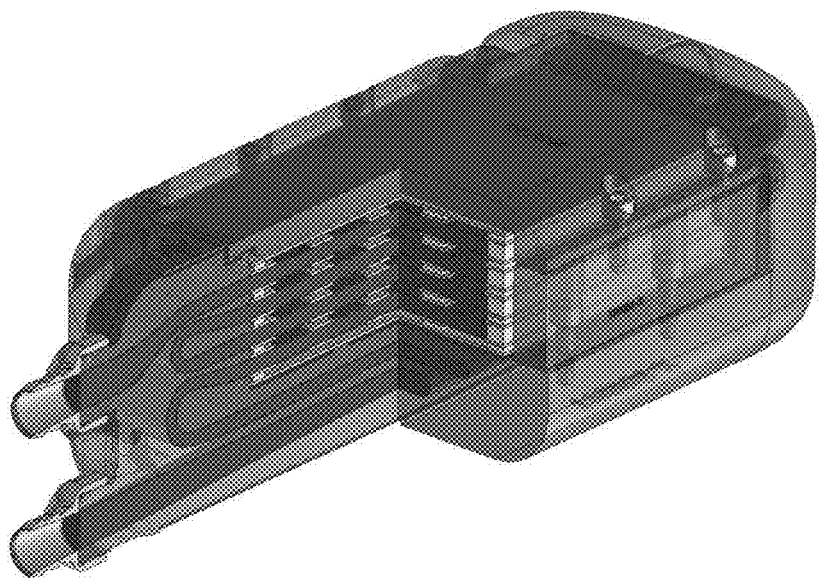
FIGS. 7A-7B.
Figure 7B:
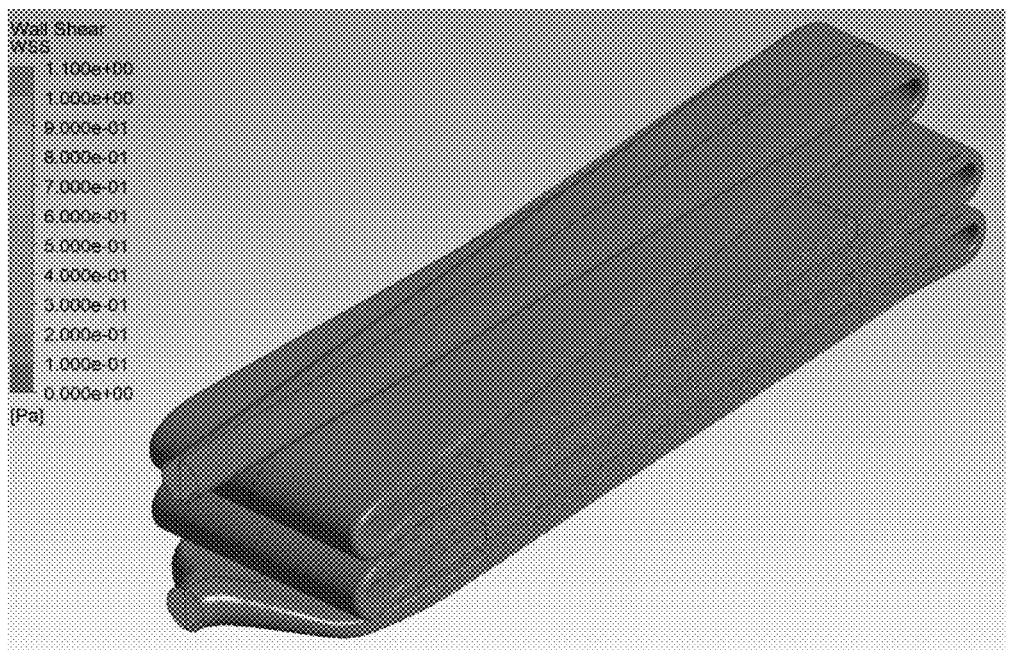

A cut out of the blood filtration device to reveal the blood flow path is depicted in FIG. 7A. FIG. 7B depict the blood flow path in the stacked membrane filter configuration. The blood flow path is defined by an extended inlet conduit; a single serpentine filtration channel; and an outlet conduit; the extended inlet conduit comprising: an inlet; a first transition region; a first turnaround section; a second transition region; a second turnaround section; wherein in the first transition region the inlet transitions from a circular cross section, configured for connection to a blood vessel of an individual, into a substantially rectangular cross section, wherein the rectangular cross section at the end of the first transition region matches the rectangular cross section of the first turnaround section, wherein in the second transition region the first turnaround section expands in width such that the rectangular cross section at the end of the second transition region matches the rectangular cross section of the second turnaround section, wherein the rectangular cross section of the second turnaround section matches that of the serpentine filtration channel; the serpentine filtration channel comprising: a plurality of filtration sections arranged in a spaced-apart stacked configuration wherein the filtration sections are connected via turnaround sections; and the outlet comprising: first region having a rectangular cross-section; and a second region that transitions from rectangular to a circular cross section and terminates in a circular outlet configured for connection to a blood vessel of a subject. The plurality of filtration sections each define a rectangular lumen enclosed by a top surface, a bottom surface, and side walls connecting the top and bottom surfaces. The top surface comprises a membrane for filtration of blood in the channel lumen and the bottom surface comprises a membrane for filtration of blood in the channel lumen. In the filtration device implanted in the porcine subject the plurality of filtration sections included 4 filtration sections.

Figure 8:
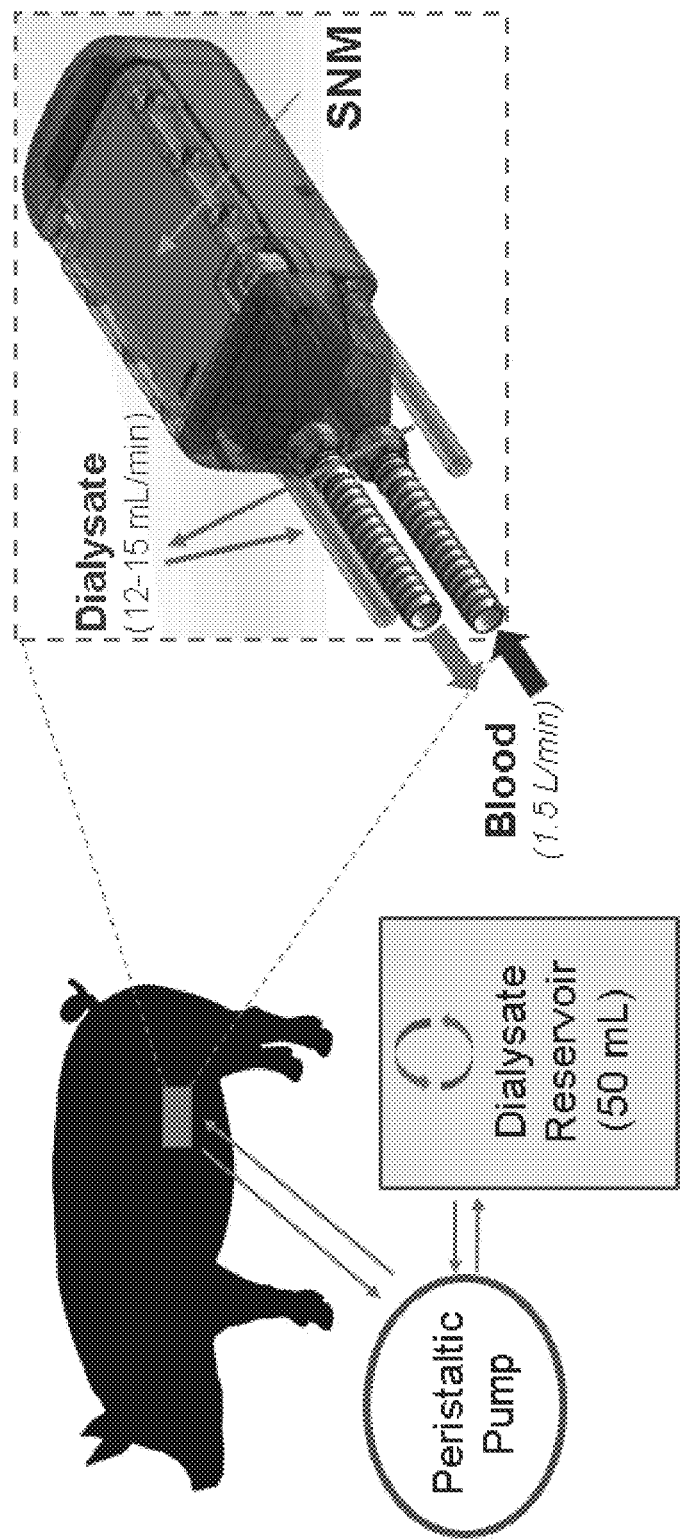
FIG. 8. Hemodialysis in porcine subject surgically implanted with a blood filtration device as provided herein.
Figure 9:
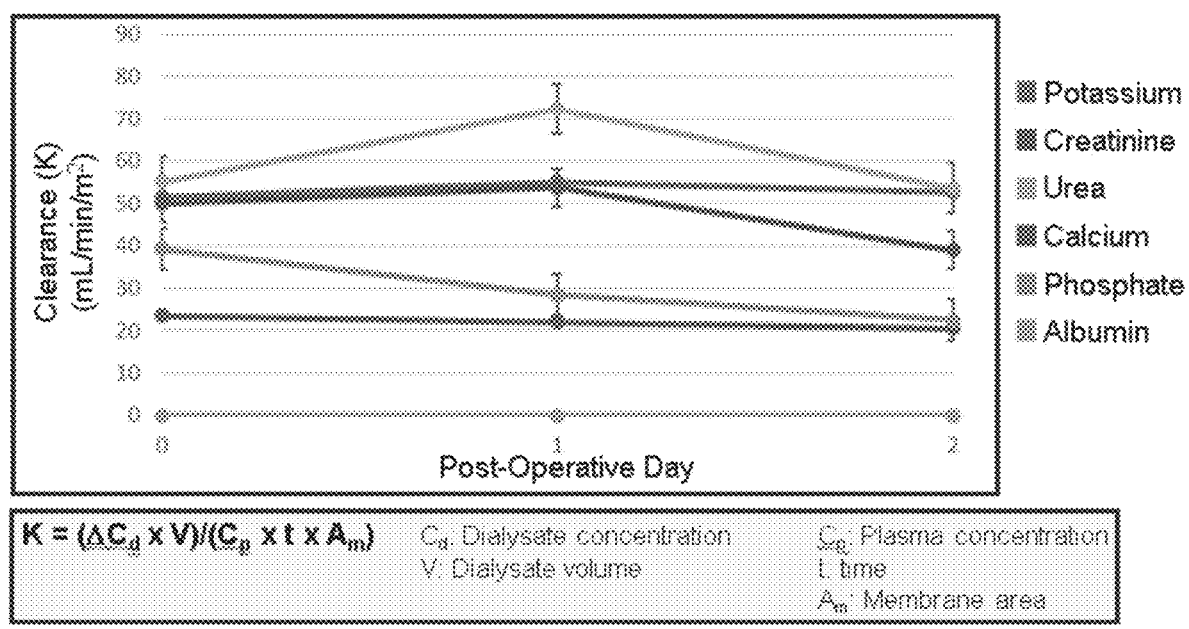
FIG. 9. Clearance of secreted molecules in porcine subject by the implanted filtration device.

Three porcine subjects were implanted with the filtration device. See FIG. 8. The filtration device successfully cleared solutes for 3 consecutive days in all three subjects. See FIG. 9.

REFERENCES

[1] W. H. Fissell, S. Roy. "The Implantable Artificial Kidney," Semin Dial. 2009; 22(6): 665-70.
[2] S. Kim, B. Feinberg, R. Kant, B. W. Chui, K. Goldman, J. Park, W. Moses, C. Blaha, Z. Iqbal, C. Chow, N. Wright, W. H. Fissell, A. Zydney, S. Roy. "Diffusive Silicon Nanopore Membranes for Hemodialysis Applications," PLoS One. 2016; 11(7): e0159526.
[3] S. Roy, A. Dubnisheva, A. Eldrige, A. J. Fleischman, K. G. Goldman, H. D. Humes, A. L. Zydney, W. H. Fissell, "Silicon Nanopore Membrane Technology for an Implantable Artificial Kidney." Proceedings of Transducers 2009, Denver, CO, USA, 2009.

Although preferred embodiments of the subject invention have been described in some detail, it is understood that obvious variations can be made without departing from the spirit and the scope of the invention as defined herein.

What is claimed is:

1. A hemofilter for use in filtering blood in vivo, the hemofilter comprising:
    stacked filtration membranes providing a plurality of flow paths for blood alternating with a plurality of flow paths for dialysate or ultrafiltrate at filtration regions of the hemofilter,
    wherein a first flow path for dialysate or ultrafiltrate is defined between a second surface of a first membrane and a first surface of a second membrane and a first flow path for blood is defined between a second surface of the second membrane and a first surface of a third membrane,
    wherein a second flow path for dialysate or ultrafiltrate is defined between a second surface of a third membrane and a first surface of a fourth membrane and a second flow path for blood is defined between a second surface of the fourth membrane and a first surface of a fifth membrane,
    wherein the flow paths for dialysate or ultrafiltrate are fluidically connected to a common channel extending along the height of the stacked membranes, the common channel fluidically communicating with an opening in each of the flow paths for dialysate or ultrafiltrate, the common channel comprising an outlet for exit of ultrafiltrate or dialysate from the hemofilter,
    wherein the flow paths for blood from filtration regions are within a continuous serpentine conduit for blood flow,
    wherein the serpentine conduit includes a plurality of substantially U-shaped regions connecting the plurality of flow paths for blood,
    wherein the serpentine conduit includes an inlet for flowing blood into a first end of the first flow path for blood and an outlet for exit of blood from the hemofilter,
    wherein a second end of the first flow path for blood is connected to a first substantially U-shaped region that is connected to a first end of the second flow path for blood.

2. The hemofilter of claim 1, wherein each of the plurality of flow paths for ultrafiltrate comprises two diagonally opposite openings, wherein a first common channel extends along the height of the stacked membranes adjacent a first corner of the stacked membranes and a second common channel extends along the height of the stacked membranes adjacent a second corner of the stacked membranes, wherein the two diagonally opposite openings are defined at two diagonally opposite corners of the flow paths for ultrafiltrate, the first common channel fluidically communicating with a first opening in each of the flow paths for ultrafiltrate, the second common channel fluidically communicating with a second opening in each of the flow paths for ultrafiltrate, the first and second common channels comprising an outlet for exit of ultrafiltrate from the hemofilter.

3. The hemofilter of claim 1, wherein each of the plurality of flow paths for dialysate comprises two diagonally opposite openings, wherein a first common channel extends along the height of the stacked membranes adjacent a first corner of the stacked membranes and a second common channel extends along the height of the stacked membranes adjacent a second corner of the stacked membranes, wherein the two diagonally opposite openings are defined at two diagonally opposite corners of the flow paths for dialysate, the first common channel fluidically communicating with a first opening in each of the flow paths for dialysate, the second common channel fluidically communicating with a second opening in each of the flow paths for dialysate, the first common channel comprising an inlet for introducing a dialysate into the hemofilter and the second common channel comprising an outlet for exit of dialysate from the hemofilter, wherein the dialysate flows from the first common channel into the openings connected to the first channel, over the flow path, and into the diagonally opposite openings and into the second common channel.

4. The hemofilter of claim 3, wherein hemofilter comprises n number of flow paths for blood and n+1 number of flow paths for dialysate/ultrafiltrate, wherein n is 2-50.

5. The hemofilter of claim 1, wherein the serpentine conduit of the hemofilter is shaped and dimensioned to provide a volumetric flow rate of 20-100 ml/min for blood flowing through the each of the filtration regions defined by the blood flow paths and wherein the hemofilter provides a total volumetric flow rate of 750-2000 ml/min for blood flowing through the hemofilter.

6. The hemofilter of claim 1, wherein each of the plurality of blood flow paths has a length of 10 mm-200 mm.

7. The hemofilter of claim 1, wherein each of the plurality of blood flow paths has a width of 5 mm-100 mm.

8. The hemofilter of claim 1, wherein each of the plurality of blood flow paths has a height of 0.5 mm-2.5 mm.

9. The hemofilter of claim 1, wherein a curvature of the plurality of substantially U-shaped regions is non-uniform.

10. The hemofilter of claim 1, wherein a curvature of the plurality of substantially U-shaped regions is circular.

11. The hemofilter of claim 1, wherein a curvature of the plurality of substantially U-shaped regions is elliptical.

12. The hemofilter of claim 1, wherein the height of the plurality of substantially U-shaped regions is non-uniform.

* * * * *